United States Patent [19]

Preiss

[11] Patent Number: 5,702,379

[45] Date of Patent: Dec. 30, 1997

[54] DISPOSABLE SANITARY ARTICLES

[76] Inventor: Shoshana Preiss, 7 Twineham Green, London N12 7ER, England

[21] Appl. No.: 414,655

[22] Filed: Mar. 30, 1995

Related U.S. Application Data

[63] Continuation-in-part of Ser. No. 141,138, Oct. 22, 1993, abandoned.

[30] Foreign Application Priority Data

Oct. 22, 1992 [GB] United Kingdom .................. 9222159

[51] Int. Cl.$^6$ .......................... A61F 13/15; A61F 13/20
[52] U.S. Cl. ........................ 604/385.1; 206/581
[58] Field of Search ........................... 604/385.1, 398; 206/438, 446, 581, 524.1, 811, 812, 823, 828

[56] References Cited

U.S. PATENT DOCUMENTS

| 4,221,221 | 9/1980 | Ehrlich | 128/284 |
|---|---|---|---|
| 4,702,378 | 10/1987 | Finkel et al. | 206/581 |
| 4,743,240 | 5/1988 | Powell | 604/385.1 |
| 4,790,840 | 12/1988 | Cortina | 604/385.1 |
| 4,931,052 | 6/1990 | Feldman | 604/385.1 |
| 5,141,505 | 8/1992 | Barrett | 604/385.1 |
| 5,241,710 | 9/1993 | Lockhart | 604/385.1 |

*Primary Examiner*—John G. Weiss
*Assistant Examiner*—Ki Yong O
*Attorney, Agent, or Firm*—Harrison & Egbert

[57] ABSTRACT

A disposable sanitary article including a first member of an absorbent material, a second member of impervious material releasably attached to the first member, and at least one third member of impervious material enclosed by the second member. The second member is in the form of a bag. The third member sealingly encloses a cleaning item. The third member is either encompassed by an exterior surface or interior surface of the second member, or formed integrally with the second member.

8 Claims, 3 Drawing Sheets

DISPOSABLE SANITARY ARTICLES

RELATED APPLICATIONS

The present application is a continuation-in-part of U.S. patent application Ser. No. 08/141,138, filed on Oct. 22, 1993, and entitled "DISPOSABLE SANITARY ARTICLES", presently pending.

TECHNICAL FIELD

This invention relates to disposable sanitary articles comprising an absorbent pad. Various forms of such articles are known, e.g. nappies (or diapers), sanitary napkins for the absorption of menstrual emissions, incontinence articles and the like.

BACKGROUND ART

Problems relating to the disposal of such sanitary articles have already been addressed in the prior art. Examples include the constructions proposed in UK Patent Publications Nos. 1518540, 2060398 and 2167375. However, none of such prior proposals is concerned with the need to clean the body area(s) before the fresh sanitary article is applied thereto in replacement of a used, usually soiled, sanitary article that has been removed. (Usually, of course, the fresh replacement sanitary article is only necessary because such body area(s), and the old sanitary article being replaced, are in a soiled state). The present invention is primarily concerned with this cleaning need.

SUMMARY OF THE INVENTION

According to one aspect of the present invention there is provided a disposable sanitary article comprising:

a first member comprising a pad of absorbent material;

a second member of impervious material in the form of a bag that is releasably attached to said first member; and at least one third member of impervious material which sealingly encloses a cleaning item, the or each said third member being itself enclosed by the said second member.

The or each said third member may be wrapped up in the said second member (i.e. be encompassed by an exterior surface of the said second member).

Alternatively the or each said third member may be disposed inside the said bag (i.e. be encompassed by an interior surface of the said second member).

The sanitary articles may be a sanitary napkin for the absorption of menstrual emissions, or an incontinence article, or (as is preferred) a nappy or diaper.

Advantageously the said pad of the first member has an outer layer of impervious material, and the said second member is attached to said outer layer by means including a releasable adhesive.

Preferably said bag is folded up in the form of a rectangle and is adhered to the said outer layer by a quick-release contact adhesive and/or by an adhesive tape that extends across one or more edges of the rectangle. Where the or each said third member is wrapped up within the folds of the said second member, the adhesive tape may serve to retain the or each said third member in its condition of enclosure by the said second member.

Advantageously the or each cleaning item is a selected one of the following (without duplication):

a cleaning cloth moistened with a volatile cleaning fluid;

talcum powder;

cleansing cream or lotion;

cream or lotion applicator (e.g. cotton wool pad).

Advantageously the edge-connected sachets are disposed in fan-folded (concertina) fashion.

DETAILED DESCRIPTION OF THE INVENTION

Figure 1:
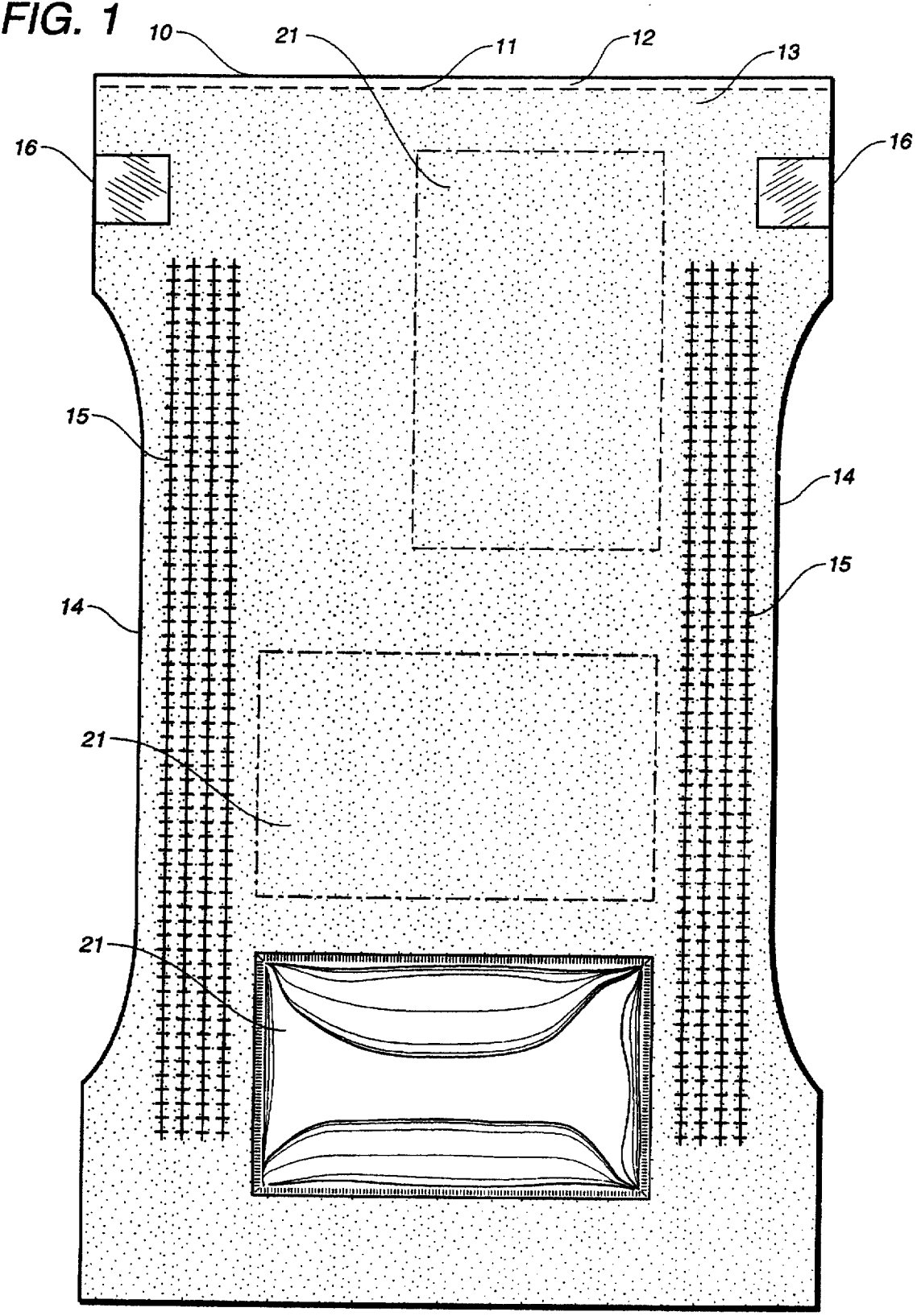
FIG. 1 is a plan view of a sanitary package according to this invention in a partly unfolded state.
Figure 3:
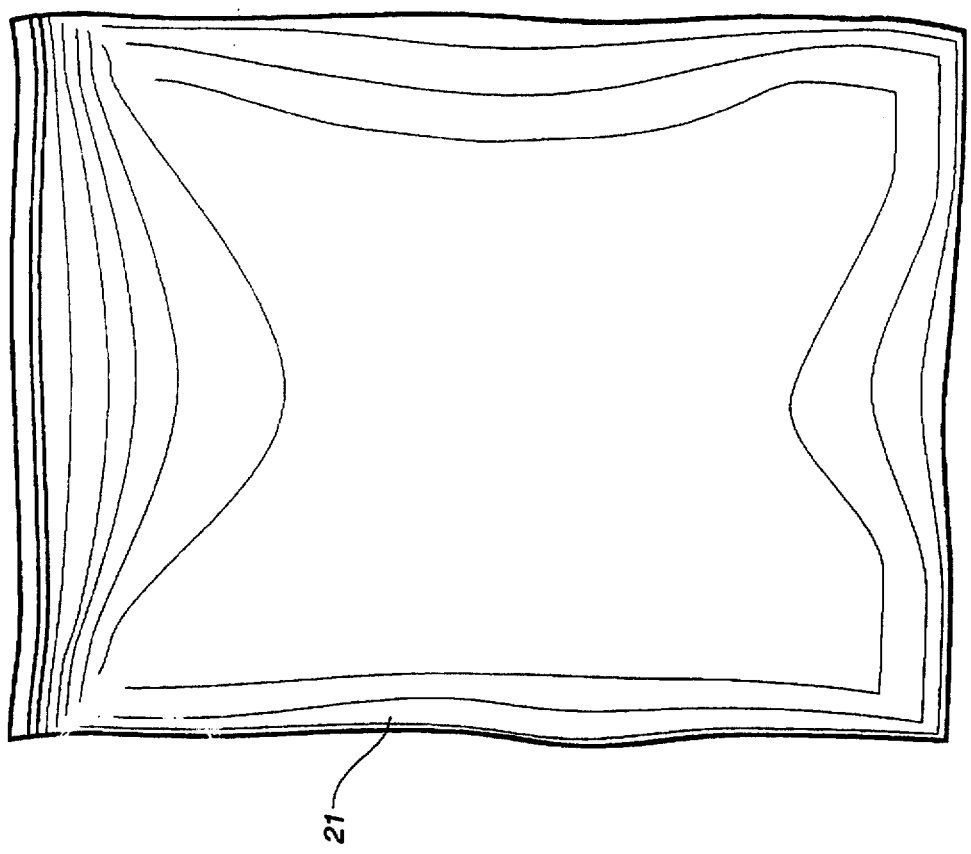
FIG. 3 is a plan view of the bag of FIG. 2 when in its unfolded state.
Figure 2:
FIG. 2 is a plan view of a bag (in folded up state) when removed from the package of FIG. 1.

The illustrated embodiment of the invention provides a single package 10 comprising three mutually combined or interconnected—though functionally separate—kinds of component articles.

The first, and main component is a disposable sanitary article in the form of an infant's nappy or diaper 11. The nappy 11 comprises a main member 12 in the form of a pad of absorbent material provided with an outer layer 13 of impervious material, the nappy having cut outs 14 in its sides adjacent elastic side strips 15, and a pair of adhesive tapes 16 adjacent one end to be fastened to the other end of the nappy when securing the nappy about the infant.

The second component is a disposal bag 21 of impervious material in rolled up or, as shown, in a folded up state and which, in its rolled-up or folded-up state, is releasably attached to the outer layer 13 of the nappy 11. This bag 21 serves to enclose the third component before the package is opened or used (i.e. as part of the package 10), and thereafter can be used as a disposal bag for a soiled nappy (e.g. that is to be replaced by the nappy 11 of this embodiment).

The third component comprises a plurality of sachets 31 each sealingly enclosing a cleaning item, the several sachets 31 being edge-connected to one another in fanfolded (concertina) fashion and being themselves enclosed by the folded-up or rolled-up bag 21.

The sachets 31 of this embodiment are formed of metallic foil or a like impervious material, and each contains a cleaning item selected (without duplication) from the following:

a cleaning cloth moistened with a volatile cleaning fluid;

a dry cloth;

cleansing cream or lotion;

a cream or lotion applicator (e.g. a cotton wool pad or wad);

talcum powder.

Figure 4:
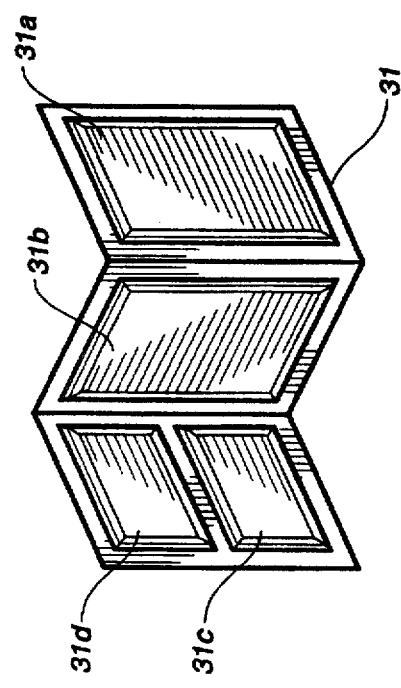
FIG. 4 is a schematic perspective view of interconnected sachets removed from the enclosing environment of the bag of FIG. 2.
Figure 5:
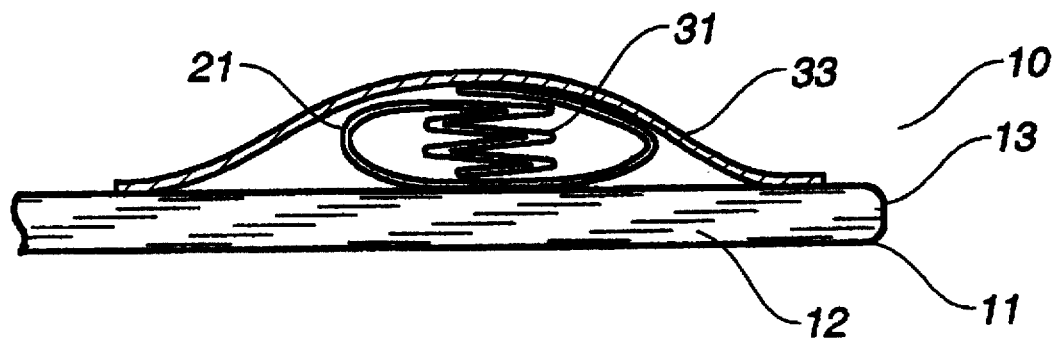
FIG. 5 is a schematic view of the present invention in its folded up state in which an adhesive tape is used to secure the bag to the layer.

For example, a full-size sachet 31a at one end contains a folded-up cleaning cloth moistened with a volatile cleaning fluid; an adjoining full-size sachet 31b contains a dry cloth; and two half-size sachets 31c and 31d (connected to the opposite edge of sachet 31b) contains respectively a cleansing cream (or lotion) and talcum powder. FIG. 4 illustrates the sachets in transparent fashion for the purpose of displaying the various cleaning items contained therein.

Figure 6:
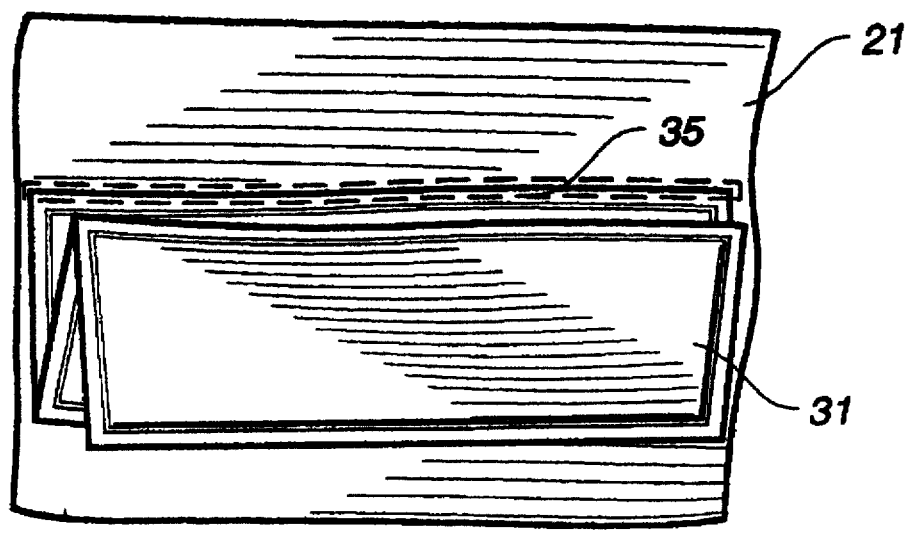
FIG. 6 shows an interior view of the bag with the sachets connected to the bag.

The fan-folded sachets 31 may be wrapped up in the rolled-up bag 21 (i.e. be encompassed by an exterior surface of the bag). Alternatively the fan-folded sachets 31 may be disposed inside the rolled-up or folded-up bag 21 (i.e. be encompassed by an interior surface of the bag). In yet another alternative, the sachets 15 may be formed integrally with the bag (e.g. where the sachets and bag are of a similar material—for example a plastics material) and conveniently in this case the sachets may be frangibly separable from the bag—e.g. via tearable perforations 35 (as shown in FIG. 6).

The bag 21 is preferably folded up in the form of a rectangle and is adhered to the outer layer 13 of the nappy 11 in the full-line position shown in FIG. 1 or in some other convenient position, e.g. one of the two alternative positions indicated by phantom lines in FIG. 1. The disposal bag 21 can have any convenient size (both in its unfolded and/or unrolled state and in its rolled-up and/or folded-up state) and can be sited in any suitable position on the nappy's outer layer 13. Attachment of bag 21 to layer 13 is by a quick-release, contact adhesive and/or by an adhesive tape 33 that extends across one or more edges of the bag. Where the fan-folded sachets 31 are wrapped up within the folds of the folded-up bag 21, the adhesive tape may serve to retain the sachets in their condition of enclosure by the bag 21.

In use the package 10 is opened to reveal the three combined articles 11, 21 and 31, the bag 21 is separated from the nappy 11 and unfolded or unrolled, and the sachets 31 are removed. The used (soiled) nappy worn by the infant is removed and placed for disposal inside the bag 21. The sachets 31a to 31d are opened and their therein-contained cleaning items used sequentially to clean the infant's soiled body areas. The used (and any remaining unused) cleaning items, as well as the empty (and any unused) sachets, are then deposited into the disposal bag 21. The fresh nappy 11 is then fastened in place about the cleaned body areas of the infant to conclude the nappy-changing operation in a clean and efficacious manner.

It will be apparent that the cleaning materials or items are provided in the sachets 31 as small one-off "doses" within the same package as the fresh nappy and the disposal bag (that is for the soiled nappy being replaced by the fresh nappy). This removes the need for the parent or child minder always to have on hand, particularly when away from home (e.g. whilest travelling, out shopping or on holiday), a number of separate large bottles, jars and other containers of the various cleaning materials which would otherwise have to be carried with the spare or replacement nappies.

Modifications and embodiments of the invention other than those described above will be readily apparent to those skilled in this art. All such modifications and embodiments are to be deemed within the ambit and scope of the invention, and the invention is not to be deemed limited to the particular embodiments) hereinbefore described which may be varied in construction and detail without departing from the scope of the patent monopoly hereby sought.

I claim:

1. A disposable sanitary article comprising:

a first member comprising a pad of absorbent material;

a second member of an impervious material in a form of a bag having an internal surface and an external surface;

releasable attachment means for releasably attaching said first member to said external surface of said bag, said bag being detachable from said first member so as to receive therewithin a soiled first member of a previously used like disposable sanitary article;

a cleaning item;

a third member of an impervious material which sealingly encloses said cleaning item, said third member being enclosed by said second member; and frangible attachment means comprising tearable perforations formed between said second member and said third member, said frangible attachment means for attaching said third member integrally to said second member such as to be unitary therewith but frangibly separable therefrom by breaking said tearable perforations of said frangible attachment means.

2. The disposable sanitary article according to claim 1, wherein said third member is wrapped up in said second member.

3. The disposable sanitary article according to claim 1, wherein said third member is disposed inside said bag.

4. The disposable sanitary article according to claim 1, wherein said pad of the first member has an outer layer of impervious material, and said releasable attachment means comprises a releasable adhesive between said outer layer and said second member.

5. The disposable sanitary article according to claim 4, wherein said bag is folded up in a form of a rectangle and said releasable adhesive is a quick-release contact adhesive.

6. The disposable sanitary article according to claim 1, wherein the cleaning item is selected from the group consisting of: a cleaning cloth moistened with a volatile cleaning fluid, a dry cloth, talcum powder, a cleansing preparation, and an applicator for a cleansing preparation.

7. The disposable sanitary article according to claim 1 comprising a plurality of cleaning items and a plurality of said third members, each of said third members containing a cleaning item which is different than another of said plurality of cleaning items.

8. The disposable sanitary article according to claim 7, wherein said plurality of cleaning items is selected, without duplication, from the group consisting of: a cleaning cloth moistened with a volatile cleaning fluid, a dry cloth, talcum powder, a cleansing preparation, and an applicator for a cleansing preparation.

* * * * *